United States Patent
Yu et al.

(10) Patent No.: US 7,709,014 B2
(45) Date of Patent: May 4, 2010

(54) HYDROXY-OLIGOCARBOXYLIC ESTERS: EFFECTS ON NERVE AND USE FOR CUTANEOUS AND MUCOCUTANEOUS ORGANS OR SITES

(76) Inventors: Ruey J. Yu, 655 Stump Rd., Chalfont, PA (US) 18914; Eugene J. Van Scott, 3 Hidden La., Abington, PA (US) 19001

( * ) Notice: Subject to any disclaimer, the term of this patent is extended or adjusted under 35 U.S.C. 154(b) by 0 days.

(21) Appl. No.: 11/548,945

(22) Filed: Oct. 12, 2006

(65) Prior Publication Data

US 2007/0093551 A1   Apr. 26, 2007

Related U.S. Application Data

(60) Provisional application No. 60/759,525, filed on Jan. 17, 2006, provisional application No. 60/727,419, filed on Oct. 17, 2005.

(51) Int. Cl.
*A61K 8/02* (2006.01)
*A61K 31/45* (2006.01)
*A61K 31/21* (2006.01)

(52) U.S. Cl. .................... 424/401; 514/844; 514/724; 514/506

(58) Field of Classification Search ............... 424/401; 514/844, 506, 553, 724
See application file for complete search history.

(56) References Cited

U.S. PATENT DOCUMENTS

| | | | |
|---|---|---|---|
| 2,277,038 A | 3/1942 | Curtis | |
| 4,813,399 A | 3/1989 | Gordon | |
| 4,959,368 A | 9/1990 | Awaya et al. | |
| 5,091,171 A | 2/1992 | Yu et al. | |
| 5,258,391 A | 11/1993 | Van Scott et al. | |
| 5,385,938 A | 1/1995 | Yu et al. | |
| 5,547,988 A | 8/1996 | Yu et al. | |
| 5,652,266 A | 7/1997 | Bobier-Rival et al. | |
| 5,665,776 A | 9/1997 | Yu et al. | |
| 5,686,489 A | 11/1997 | Yu et al. | |
| 5,889,054 A | 3/1999 | Yu et al. | |
| 6,060,512 A | 5/2000 | Yu et al. | |
| 6,191,167 B1 | 2/2001 | Yu et al. | |
| 6,217,885 B1* | 4/2001 | Roder et al. | 424/401 |
| 6,335,023 B1 | 1/2002 | Yu et al. | |
| 6,444,212 B1* | 9/2002 | Cavazzuti et al. | 424/401 |
| 6,740,327 B2 | 5/2004 | Yu et al. | |
| 6,767,924 B2 | 7/2004 | Yu et al. | |
| 2003/0175349 A1 | 9/2003 | Garg et al. | |
| 2004/0180032 A1* | 9/2004 | Manelski et al. | 424/70.121 |
| 2006/0110415 A1* | 5/2006 | Gupta | 424/401 |
| 2006/0280795 A1 | 12/2006 | Penhasi et al. | |

FOREIGN PATENT DOCUMENTS

EP    1469824 B1    9/2005

OTHER PUBLICATIONS

Yu, Ruey J. et al.; "Alphar-hydroxyacids and Carboxylic Acids"; Journal of Cosmetic Dermatology; Apr. 2004, vol. 3, No. 2, Apr. 2004, pp. 76-87.
Supplementary European Search Report for the related European Application No. 06825937 issued on Nov. 16, 2009.

* cited by examiner

*Primary Examiner*—Sreeni Padmanabhan
*Assistant Examiner*—Shobha Kantamneni
(74) *Attorney, Agent, or Firm*—Panitch Schwarze Belisario & Nadel LLP

(57) ABSTRACT

A composition and method for producing a beneficial effect on a subject's nerve associated with at least one of a cosmetic condition, a dermatological indication and a dental indication and another condition. The composition comprises a hydroxy-oligocarboxylic ester and is formulated for topical administration of the product to a subject to produce the beneficial effect. The method includes topically applying to the subject in a region where the beneficial effect is desired a hydroxy-oligocarboxylic ester in an amount effective to produce the beneficial effect.

7 Claims, No Drawings

HYDROXY-OLIGOCARBOXYLIC ESTERS: EFFECTS ON NERVE AND USE FOR CUTANEOUS AND MUCOCUTANEOUS ORGANS OR SITES

CROSS-REFERENCE TO RELATED APPLICATIONS

This application is entitled to priority pursuant to 35 U.S.C. §119(e) to U.S. Provisional Patent Application No. 60/727,419, filed Oct. 17, 2005, and to U.S. Provisional Patent Application No. 60/759,525, filed Jan. 17, 2006.

BACKGROUND OF THE INVENTION

This application relates to use of a composition comprising a hydroxy-oligocarboxylic ester for topical administration to alleviate or improve cosmetic conditions, dental conditions, dermatological indications and other conditions in which the effects on the nervous system can be beneficial, particularly with respect to sensuous and mild anesthetic properties.

U.S. Pat. No. 5,091,171, entitled "Amphoteric Compositions and Polymeric Forms of Alpha Hydroxyacids, and Their Therapeutic Use," describes preventive as well as therapeutic treatments to alleviate cosmetic conditions and symptoms of dermatologic disorders with amphoteric compositions containing alpha hydroxyacids, alpha ketoacids related compounds or polymeric forms of hydroxyacids. U.S. Pat. No. 5,547,988, entitled "Alleviating Signs of Dermatological Aging with Glycolic Acid, Lactic Acid or Citric Acid," describes the use of alpha-hydroxyacids to alleviate or improve signs of skin, nail and hair changes associated with intrinsic or extrinsic aging. U.S. Pat. No. 5,385,938, entitled "Method of Using Glycolic Acid for Treating Wrinkles," describes the use of glycolic acid for topical treatment of wrinkles. U.S. Pat. No. 5,258,391, entitled "Phenyl Alpha Acyloxyalkanoic Acids, Derivatives and Their Therapeutic Use," describes the use of topical compositions containing phenyl alpha acyloxyalkanoic acids and derivatives to enhance the keratinization of nails, skin, lips and other mucous membranes.

U.S. Pat. No. 5,665,776, entitled "Additives Enhancing Topical Actions of Therapeutic Agents," describes the use of hydroxycarboxylic acids to enhance the therapeutic effects of cosmetic or pharmaceutical agents. U.S. Pat. No. 5,686,489, entitled "Alpha Hydroxyacid Esters for Skin Aging," describes the use of alpha-hydroxyacid esters to increase skin thickness by stimulating biosynthesis of dermal components such as glycosaminoglycans, proteoglycans, collagen and elastin, and to treat aging related integumental changes including age spots, skin lines, wrinkles, photoaging and aging skin. U.S. Pat. No. 5,889,054, entitled "Method of Using Beta Hydroxyacids for Treating Wrinkles," describes the use of compositions comprising a beta-hydroxyacid for topical treatment of skin changes associated with aging. U.S. Pat. No. 6,060,512, entitled "Method of Using Hydroxycarboxylic Acids or Related Compounds for Treating Skin Changes Associated with Intrinsic and Extrinsic Aging," describes the use of compositions comprising a hydroxycarboxylic acid for topical treatment of skin changes associated with intrinsic and extrinsic aging. U.S. Pat. Nos. 6,335,023 and 6,740,327, both entitled "Oligosaccharide Aldonic Acids and Their Topical Use," describe the use of compositions comprising an oligosaccharide aldonic acid for topical treatment of cosmetic conditions and dermatological disorders. U.S. Pat. No. 6,767,924, entitled "Method of Using Hydroxycarboxylic Acids or Related Compounds for Treating Skin Changes Associated with Intrinsic and Extrinsic Aging," describes the use of compositions comprising a polyhydroxy acid in an amphoteric system for topical treatment of skin changes associated with intrinsic and extrinsic aging.

None of the above patents has described or implied actions or effects on a nerve or nerves by topical administration of a hydroxyoligocarboxylic ester, such as a hydroxydicarboxylic ester or a hydroxytricarboxylic ester.

BRIEF SUMMARY OF THE INVENTION

While a hydroxy-monocarboxylic ester does not have effects on nerves, one aspect of the invention is based on the discovery of sensuous and mild anesthetic effects produced by a hydroxy-oligocarboxylic ester, preferably a hydroxydicarboxylic ester and more preferably a hydroxytricarboxylic ester, after topical application to mucocutaneous organs or sites such as lips, and the use for cosmetic or dental conditions, dermatological indications or another condition in which the effects on the nervous system can be beneficial.

Another aspect of the invention is a method of using a composition comprising a hydroxy-oligocarboxylic ester for topical administration to alleviate or improve a disorder, symptom or syndrome associated with a nervous, cutaneous or dental system including pain, pruritus, inflammation, erythema, dermatitis, eczema, psoriasis, and in wound healing. The hydroxy-oligocarboxylic esters, preferably hydroxydicarboxylic esters and more preferably the hydroxytricarboxylic esters, are anti-oxidant neutral compounds which include, for example, diethyl tartarate, triethyl citrate, tripropyl citrate and tri-isopropyl citrate.

Still another aspect of the invention is a method for producing a beneficial effect on a subject's nerve associated with at least one of a cosmetic condition, a dermatological indication and a dental indication and another condition, the method comprising topically applying to the subject in a region where the beneficial effect is desired a hydroxy-oligocarboxylic ester in an amount effective to produce the beneficial effect.

Yet another aspect is a method for producing a beneficial effect on a subject's nerve associated with at least one of a cosmetic condition, a dermatological indication and a dental indication and another condition, the method comprising topically applying to the subject in a region where the beneficial effect is desired a hydroxy-oligocarboxylic ester in an amount effective to produce the beneficial effect, wherein the beneficial effect is at least one of a sensuous effect and a mild anesthetic effect on the nerve.

DEFINITIONS

As used herein, the singular forms "a", "an", and "the" include plural referents unless the context clearly dictates otherwise. For example, reference to a disorder, condition, indication, symptom or syndrome means one or more such disorders, conditions, indications, symptoms or syndromes.

As used herein, the term "beneficial effect" means an effect that is desired for an intended benefit, whether an inhibitory effect to prevent or alleviate a condition, or a desired positive effect, such as an enhanced and typically pleasurable sensuous or sensational or arousal effect.

As used herein, a "mild anesthetic effect" is an effect in which the anesthetized nerve, organ or tissue still has some degree of feeling, such that the degree of feeling has a beneficial effect.

As used herein, a "sensuous effect" is an effect in feeling of arousing or preoccupying with gratification of the senses, and the degree of feeling has a beneficial effect.

As used herein, the terms "treatment," "treating," and the like, refer to obtaining a desired beneficial effect, which may be a pharmacologic, physiologic, dermatologic and/or sensuous effect. The beneficial effect may be prophylactic in terms of completely or partially preventing a condition or disease or symptom thereof and/or may be therapeutic in terms of a partial or complete cure for a condition or disease and/or adverse affect attributable to the condition or disease, and/or causing an enhanced sensuous effect in the case of a sensuous treatment. "Treatment" or "treating" thus, for example, covers any treatment of a condition or disease in an animal, preferably in a mammal, and more preferably in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease; all in the case where the beneficial effect is a desired inhibitory effect. "Treatment" or "treating" also includes creating the existence of or enhancing a sensuous condition where the beneficial effect is a desired positive enhancement of a sensuous, sensational or arousal effect.

DETAILED DESCRIPTION OF THE INVENTION

The present invention is based on the discovery that topical application of a hydroxy-oligocarboxylic ester, preferably a hydroxydicarboxylic ester or more preferably a hydroxytricarboxylic ester such as tripropyl citrate on topical application can produce sensuous, sensational and mild anesthetic effects on mucocutaneous organs or sites, such as lips, mouth, gum, nostrils, nipples, vulva, vagina, penis and anus. We have also found in contrast that a hydroxy-monocarboxylic ester, such as ethyl glycolate and ethyl lactate does not produce a sensuous or mild anesthetic effect under the same conditions. The sensuous and sensational effects produced by the hydroxy-oligocarboxylic ester, preferably a hydroxydicarboxylic ester or more preferably a hydroxytricarboxylic ester are quite different from the numbing effects induced by local anesthetics such as lidocaine and procaine. The sensuous, sensational and mild anesthetic effects produced by the hydroxy-oligocarboxylic ester according to the present invention generally last from a few minutes to a few hours. Such nerve-acting sensation or effect has many cosmetic, dental and dermatological applications. For example, a lipstick or lip balm comprising a hydroxy-oligocarboxylic ester, preferably a hydroxydicarboxylic ester or more preferably a hydroxytricarboxylic ester, can provide a sensuous or sensational feeling after topical application to lips of a human subject. Such sensuous action and certain anesthetic effects on nervous system produced by the hydroxy-oligocarboxylic ester can have beneficial applications such as to relieve itch or pain of lips, mouth, gum, nostrils, nipples, vulva, vagina, penis and anus, and for conditions associated with eczema, hemorrhoids, dry or aging-associated changes of the vulva and vagina.

One aspect of the invention is a method for producing a beneficial effect on a subject's nerve associated with at least one of a cosmetic condition, a dermatological indication and a dental indication and another condition, the method comprising topically applying to the subject in a region where the beneficial effect is desired a hydroxy-oligocarboxylic ester in an amount effective to produce the beneficial effect.

Another aspect is a method for producing a beneficial effect on a subject's nerve associated with at least one of a cosmetic condition, a dermatological indication and a dental indication and another condition, the method comprising topically applying to the subject in a region where the beneficial effect is desired a hydroxy-oligocarboxylic ester in an amount effective to produce the beneficial effect, wherein the beneficial effect is at least one of a sensuous effect and a mild anesthetic effect on the nerve.

The hydroxy-oligocarboxylic ester includes at least one of diethyl malate, triethyl citrate, tripropyl citrate, tri-isopropyl citrate, diethyl glucate and dipropyl glucate, and any combination thereof.

Another aspect of the invention is the use of a hydroxy-oligocarboxylic ester, preferably a hydroxydicarboxylic ester or more preferably a hydroxytricarboxylic ester, to heal and relieve pains, infections, inflammations associated with wound healing and disorders of mucocutaneous organs or sites such as canker sores and toothache. For the mouth diseases, the hydroxy-oligocarboxylic ester is formulated as a solution or gel for mouth wash, gargle or rubbing.

The hydroxy-oligocarboxylic ester of the present invention is an anti-oxidant neutral compound. Yet another aspect of the invention is the use of the anti-oxidant hydroxy-oligocarboxylic ester, preferably a hydroxydicarboxylic ester or more preferably a hydroxytricarboxylic ester, as preventive care or treatment for damage, stinging or irritation of mucocutaneous organs or sites, skin, hair or nails caused by sunlight, chemicals, laser treatment, free radicals, electromagnetic radiation, ionizing radiation such as alpha rays, beta rays, X-rays, gamma rays or other oxidative damages.

Yet another aspect of the invention is the use of a hydroxy-oligocarboxylic ester on cutaneous or mucocutaneous organs, sites or lesions for topical prevention or treatment of cosmetic conditions or dermatological indications selected from the group consisting of acne; rosacea; blemished skin; cellulite; dermatoses; dermatitis; skin or nail infections; dandruff; dry skin; xerosis; eczema; herpes; ichthyosis; pseudofolliculitis barbae; pruritus; psoriasis; stretch marks; warts; oral or gum disease; irritated, inflamed, unhealthy, damaged or abnormal mucosa, skin, hair, nail, nostril, ear canal, anal or vaginal conditions; uneven and rough surface of skin, nail and hair; reactive, irritating or telangiectatic skin; for skin bleach and lightening; and wound healing.

The hydroxy-oligocarboxylic esters of the present invention represent a group of organic compounds which contain one or more hydroxyl groups and two to ten carboxyl groups in the molecules. The preferred hydroxy-oligocarboxylic esters contain one or more hydroxyl groups and two to three carboxyl groups in the molecules. The most preferred hydroxy-oligocarboxylic esters contain one or more hydroxyl groups and three carboxyl groups in the molecules, such as triethyl citrate and tripropyl citrate.

The hydroxy-oligocarboxylic esters of the present invention can be described as follows.

(A) Hydroxydicarboxylic Ester

Hydroxydicarboxylic ester can be divided into two groups; one is monohydroxydicarboxylic ester and the other is dihydroxydicarboxylic ester.

(1) Monohydroxydicarboxylic Ester

Monohydroxydicarboxylic ester comprises one hydroxyl group and two carboxyl groups. The generic structure can be represented as the following Formula I:

$$R_1OOC\ C(OH)R_2\ CHR_4\ COOR_3 \qquad (I)$$

wherein $R_1$ and $R_3$ are independently an alkyl group having 1 to 19 carbon atoms, or an aralkyl or aryl group having 6 to 19 carbon atoms; $R_2$ and $R_4$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The monohydroxydicarboxylic ester can be present as saturated or unsaturated, stereoisomeric or non-stereoisomeric, straight or branched chain or cyclic form.

If the generic structure of Formula I cannot cover a specific monohydroxydicarboxylic ester, the compound will be represented by its chemical name.

The following are representative hydroxydicarboxylic esters:

2-hydroxybutane-1,4-dioate esters (malate esters): dimethyl malate, diethyl malate, dipropyl malate, di-isopropyl malate, diamyl malate, dioctyl malate, di-isooctyl malate and dibenzyl malate.

2-hydroxy-2-methyl-butane-1,4-dioate esters (citramalate esters): dimethyl citramalate, diethyl citramalate, dipropyl citramalate, di-isopropyl citramalate, diamyl citramalate, dioctyl citramalate, di-isooctyl citramalate and dibenzyl citramalate.

(2) Dihydroxydicarboxylic Ester

Dihydroxydicarboxylic ester comprises two hydroxyl groups and two carboxyl groups. The generic structure can be represented as the following Formula II:

$$R_1OOC\ C(OH)R_2\ C(OH)R_4\ COOR_3 \quad (II)$$

wherein $R_1$ and $R_3$ are independently an alkyl group having 1 to 19 carbon atoms, or an aralkyl or aryl group having 6 to 19 carbon atoms; $R_2$ and $R_3$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The dihydroxydicarboxylic ester can be present as saturated or unsaturated, stereoisomeric or non-stereoisomeric, straight or branched chain or cyclic form.

If the generic structure of Formula II cannot cover a specific dihydroxydicarboxylic ester, the compound will be represented by its chemical name.

The following are representative dihydroxydicarboxylic esters:

2,3-dihydroxybutane-1,4-dioate esters (tartarate esters): dimethyl tartarate, diethyl tartarate, dipropyl tartarate, di-isopropyl tartarate, diamyl tartarate, dioctyl tartarate, di-isooctyl tartarate and dibenzyl tartarate.

(B) Hydroxytricarboxylic Ester

Hydroxytricarboxylic ester can be divided into three groups; (1) monohydroxytricarboxylic ester, (2) dihydroxytricarboxylic ester and (3) trihydroxytricarboxylic ester.

(1) Monohydroxytricarboxylic Ester

Monohydroxytricarboxylic ester comprises one hydroxyl group and three carboxyl groups, and can be divided into four groups, (a) citrate ester, (b) isocitrate ester, (c) homocitrate ester and (d) homoisocitrate ester.

(a) Citrate Ester

The generic structure of citrate ester can be represented as the following Formula III:

$$R_1OOC\ CHR_2\ C(OH)(COOR_3)\ CHR_4\ COOR_5 \quad (III)$$

wherein $R_1$, $R_3$ and $R_5$ are independently an alkyl group having 1 to 19 carbon atoms, or an aralkyl or aryl group having 6 to 19 carbon atoms; $R_2$ and $R_4$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The citrate ester can be present as saturated or unsaturated, stereoisomeric or non-stereoisomeric, straight or branched chain or cyclic form.

If the generic structure of Formula III cannot cover a specific citrate ester, the compound will be represented by its chemical name.

The following are representative citrate esters:

3-hydroxy-3-carboxypentane-1,5-dioate esters (citrate esters): trimethyl citrate, triethyl citrate, tripropyl citrate, tri-isopropyl citrate, triamyl citrate, trioctyl citrate, tri-isooctyl citrate, tribenzyl citrate and trinicotinyl citrate.

2-n-hexadecyl-3-hydroxy-3-carboxypentane-1,5-dioate esters (agaricate esters, n-hexadecyl citrate esters): trimethyl agaricate, triethyl agaricate, tripropyl agaricate, tri-isopropyl agaricate, triamyl agaricate, trioctyl agaricate, tri-isooctyl agaricate, tribenzyl agaricate and trinicotinyl agaricate.

(b) Isocitrate Ester

The generic structure of isocitrate ester can be represented as the following Formula IV:

$$R_1OOC\ C(OH)R_2\ CR_4(COOR_3)\ CHR_6\ COOR_5 \quad (IV)$$

wherein $R_1$, $R_3$ and $R_5$ are independently an alkyl group having 1 to 19 carbon atoms, or an aralkyl or aryl group having 6 to 19 carbon atoms; $R_2$, $R_4$ and $R_6$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The isocitrate ester can be present as saturated or unsaturated, stereoisomeric or non-stereoisomeric, straight or branched chain or cyclic form.

If the generic structure of Formula IV cannot cover a specific isocitrate ester, the compound will be represented by its chemical name.

The following are representative isocitrate esters:

2-hydroxy-3-carboxypentane-1,5-dioate esters (isocitrate esters): trimethyl isocitrate, triethyl isocitrate, tripropyl isocitrate, tri-isopropyl isocitrate, triamyl isocitrate, trioctyl isocitrate, tri-isooctyl isocitrate, tribenzyl isocitrate and trinicotinyl isocitrate.

(c) Homocitrate Ester

The generic structure of homocitrate ester can be represented as the following Formula V:

$$R_1OOC\ CHR_2\ C(OH)(COOR_3)\ CHR_4\ CHR_6\ COOR_5 \quad (V)$$

wherein $R_1$, $R_3$ and $R_5$ are independently an alkyl group having 1 to 19 carbon atoms, or an aralkyl or aryl group having 6 to 19 carbon atoms; $R_2$, $R_4$ and R6 are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The homocitrate ester can be present as saturated or unsaturated, stereoisomeric or non-stereoisomeric, straight or branched chain or cyclic form.

If the generic structure of Formula V cannot cover a specific homocitrate ester, the compound will be represented by its chemical name.

The following are representative homocitrate esters:

3-hydroxy-3-carboxyhexane-1,6-dioate esters (homocitrate esters): trimethyl homocitrate, triethyl homocitrate, tripropyl homocitrate, tri-isopropyl homocitrate, triamyl homocitrate, trioctyl homocitrate, tri-isooctyl homocitrate, tribenzyl homocitrate and trinicotinyl homocitrate.

(d) Homoisocitrate Ester

The generic structure of homoisocitrate ester can be represented as the following Formula VI:

$$R_1OOC\ C(OH)R_2\ CR_4(COOR_3)\ CHR_6\ CHR_7\ COOR_5 \quad (VI)$$

wherein $R_1$, $R_3$ and $R_5$ are independently an alkyl group having 1 to 19 carbon atoms, or an aralkyl or aryl group having 6 to 19 carbon atoms; $R_2$, $R_4$, $R_6$ and $R_7$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The homoisocitrate ester can be present as saturated or unsaturated, stereoisomeric or non-stereoisomeric, straight or branched chain or cyclic form.

If the generic structure of Formula VI cannot cover a specific homoisocitrate ester, the compound will be represented by its chemical name.

The following are representative homoisocitrate esters:
2-hydroxy-3-carboxyhexane-1,6-dioate esters (homoisocitrate esters): trimethyl homoisocitrate, triethyl homoisocitrate, tripropyl homoisocitrate, tri-isopropyl homoisocitrate, triamyl homoisocitrate, trioctyl homoisocitrate, tri-isooctyl homoisocitrate, tribenzyl homoisocitrate and trinicotinyl homoisocitrate.

(2) Dihydroxytricarboxylic Ester

Dihydroxytricarboxylic ester comprises two hydroxyl groups and three carboxyl groups. There are five subgroups of dihydroxytricarboxylic esters: (a) hydroxycitrate ester; (b) hydroxyisocitrate ester; (c) hydroxyhomocitrate ester; (d) hydroxyhomoisocitrate ester; and (e) 4,5-dihydroxy-3-carboxyhexane-1,6-dioate ester.

(a) Hydroxycitrate ester

The generic structure can be represented as the following Formula VII:

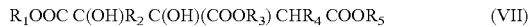
(VII)

wherein $R_1$, $R_3$ and $R_5$ are independently an alkyl group having 1 to 19 carbon atoms, or an aralkyl or aryl group having 6 to 19 carbon atoms; $R_2$ and $R_4$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The hydroxycitrate ester can be present as saturated or unsaturated, stereoisomeric or non-stereoisomeric, straight or branched chain or cyclic form.

If the generic structure of Formula VII cannot cover a specific hydroxycitrate ester, the compound will be represented by its chemical name.

The following are representative hydroxycitrate esters:
2,3-dihydroxy-3-carboxypentane-1,5-dioate esters (hydroxycitrate esters): trimethyl hydroxycitrate, triethyl hydroxycitrate, tripropyl hydroxycitrate, tri-isopropyl hydroxycitrate, triamyl hydroxycitrate, trioctyl hydroxycitrate, tri-isooctyl hydroxycitrate, tribenzyl hydroxycitrate and trinicotinyl hydroxycitrate.

2-n-hexadecyl-2,3-dihydroxy-3-carboxypentane-1,5-dioate esters and 4-n-hexadecyl-2,3-dihydroxy-3-carboxypentane-1,5-dioate esters (hydroxyagaricate esters, n-hexadecyl hydroxycitrate esters): trimethyl hydroxyagaricate, triethyl hydroxyagaricate, tripropyl hydroxyagaricate, tri-isopropyl hydroxyagaricate, triamyl hydroxyagaricate, trioctyl hydroxyagaricate, tri-isooctyl hydroxyagaricate, tribenzyl hydroxyagaricate and trinicotinyl hydroxyagaricate.

(b) Hydroxyisocitrate ester

The generic structure can be represented as the following Formula VIII:

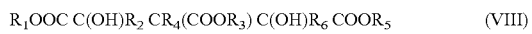
(VIII)

wherein $R_1$, $R_3$ and $R_5$ are independently an alkyl group having 1 to 19 carbon atoms, or an aralkyl or aryl group having 6 to 19 carbon atoms; $R_2$, $R_4$ and $R_6$ are independently H, an alkyl group having 1 to 19 carbon atoms, or an aralkyl or aryl group having 6 to 19 carbon atoms; the H attached to any carbon atom can be substituted by I, F, Cl, Br or alkoxyl group having 1 to 19 carbons. The hydroxyisocitrate ester can be present as saturated or unsaturated, stereoisomeric or non-stereoisomeric, straight or branched chain or cyclic form.

If the generic structure of Formula VIII cannot cover a specific hydroxyisocitrate ester, the compound will be represented by its chemical name.

The following are representative hydroxyisocitrate esters.
2,4-dihydroxy-3-carboxypentane-1,5-dioate esters (hydroxyisocitrate esters): trimethyl hydroxyisocitrate, triethyl hydroxyisocitrate, tripropyl hydroxyisocitrate, tri-isopropyl hydroxyisocitrate, triamyl hydroxyisocitrate, trioctyl hydroxyisocitrate, tri-isooctyl hydroxyisocitrate, tribenzyl hydroxyisocitrate and trinicotinyl hydroxyisocitrate.

(c) Hydroxyhomocitrate ester

Due to the position of the second hydroxyl group, there are three generic structures which can be represented as the following Formulas IX, X and XI:

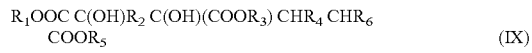
(IX)

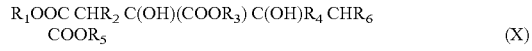
(X)

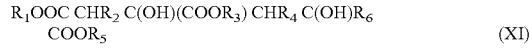
(XI)

wherein, in each of the Formulas IX, X and XI, $R_1$, $R_3$ and $R_5$ are independently an alkyl group having 1 to 19 carbon atoms, or an aralkyl or aryl group having 6 to 19 carbon atoms; $R_2$, $R_4$ and $R_6$ are independently H, an alkyl group having 1 to 19 carbon atoms, or an aralkyl or aryl group having 6 to 19 carbon atoms; the H attached to any carbon atom can be substituted by I, F, Cl, Br or alkoxyl group having 1 to 19 carbons. The hydroxyhomocitrate ester can be present as saturated or unsaturated, stereoisomeric or non-stereoisomeric, straight or branched chain or cyclic form.

If the generic structures of Formulas IX, X or XI cannot cover a specific hydroxyhomocitrate ester, the compound will be represented by its chemical name.

The following are representative hydroxyhomocitrate esters:
2,3-dihydroxy-3-carboxyhexane-1,6-dioate esters; 3,4-dihydroxy-3-carboxyhexane-1,6-dioate esters; and 3,5-dihydroxy-3-carboxyhexane-1,6-dioate esters (hydroxyhomocitrate esters): trimethyl hydroxyhomocitrate, triethyl hydroxyhomocitrate, tripropyl hydroxyhomocitrate, tri-isopropyl hydroxyhomocitrate, triamyl hydroxyhomocitrate, trioctyl hydroxyhomocitrate, tri-isooctyl hydroxyhomocitrate, tribenzyl hydroxyhomocitrate and trinicotinyl hydroxyhomocitrate.

(d) Hydroxyhomoisocitrate ester

Due to the position of the second hydroxyl group, there are two generic structures which can be represented as the following Formulas XII and XIII:

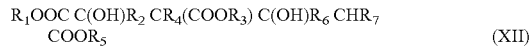
(XII)

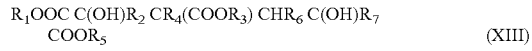
(XIII)

wherein in each of the Formulas XII and XIII, $R_1$, $R_3$ and $R_5$ are independently an alkyl group having 1 to 19 carbon atoms, or an aralkyl or aryl group having 6 to 19 carbon atoms; $R_2$, $R_4$, $R_6$ and $R_7$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The hydroxyhomoisocitrate ester can be present as saturated or unsaturated, stereoisomeric or non-stereoisomeric, straight or branched chain or cyclic form.

If the generic structures of Formulas XII or XIII cannot cover a specific hydroxyhomoisocitrate ester, the compound will be represented by its chemical name.

The following are representative hydroxyhomoisocitrate esters:

2,4-dihydroxy-3-carboxyhexane-1,6-dioate esters and 2,5-dihydroxy-3-carboxyhexane-1,6-dioate esters (hydroxyhomoisocitrate esters): trimethyl hydroxyhomoisocitrate, triethyl hydroxyhomoisocitrate, tripropyl hydroxyhomoisocitrate, tri-isopropyl hydroxyhomoisocitrate, triamyl hydroxyhomoisocitrate, trioctyl hydroxyhomoisocitrate, tri-isooctyl hydroxyhomoisocitrate, tribenzyl hydroxyhomoisocitrate and trinicotinyl hydroxyhomoisocitrate.

(e) 4,5-dihydroxy-3-carboxyhexane-1,6-dioate ester

The generic structure can be represented as the following Formula XIV:

$$R_1OOC\ CHR_2\ CR_4(COOR_3)\ C(OH)R_6\ C(OH)R_7\ COOR_5 \qquad (XIV)$$

wherein, $R_1$, $R_3$ and $R_5$ are independently an alkyl group having 1 to 19 carbon atoms, or an aralkyl or aryl group having 6 to 19 carbon atoms; $R_2$, $R_4$, $R_6$ and $R_7$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The 4,5-dihydroxy-3-carboxyhexane-1,6-dioate esters can be present as saturated or unsaturated, stereoisomeric or non-stereoisomeric, straight or branched chain or cyclic form.

If the generic structure of Formula XIV cannot cover a specific 4,5-dihydroxy-3-carboxyhexane-1,6-dioate ester, the compound will be represented by its chemical name.

The following are representative 4,5-dihydroxy-3-carboxyhexane-1,6-dioate esters: trimethyl 4,5-dihydroxy-3-carboxyhexane-1,6-dioate; triethyl 4,5-dihydroxy-3-carboxyhexane-1,6-dioate; tripropyl 4,5-dihydroxy-3-carboxyhexane-1,6-dioate; tri-isopropyl 4,5-dihydroxy-3-carboxyhexane-1,6-dioate; triamyl 4,5-dihydroxy-3-carboxyhexane-1,6-dioate; trioctyl 4,5-dihydroxy-3-carboxyhexane-1,6-dioate; tri-isooctyl 4,5-dihydroxy-3-carboxyhexane-1,6-dioate; tribenzyl 4,5-dihydroxy-3-carboxyhexane-1,6-dioate and trinicotinyl 4,5-dihydroxy-3-carboxyhexane-1,6-dioate.

(3) Trihydroxytricarboxylic Ester

Trihydroxytricarboxylic ester comprises three hydroxyl groups and three carboxyl groups. There are three subgroups of trihydroxytricarboxylic esters: (a) dihydroxycitrate ester, (b) dihydroxyhomocitrate ester and (c) dihydroxyhomoisocitrate ester.

(a) Dihydroxycitrate ester

The generic structure can be represented as the following Formula XV:

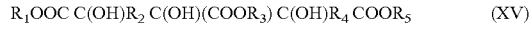

$$R_1OOC\ C(OH)R_2\ C(OH)(COOR_3)\ C(OH)R_4\ COOR_5 \qquad (XV)$$

wherein $R_1$, $R_3$ and $R_5$ are independently an alkyl group having 1 to 19 carbon atoms, or an aralkyl or aryl group having 6 to 19 carbon atoms; $R_2$ and $R_4$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The dihydroxycitrate ester can be present as saturated or unsaturated, stereoisomeric or non-stereoisomeric, straight or branched chain or cyclic form.

If the generic structure of Formula XV cannot cover a specific dihydroxycitrate ester, the compound will be represented by its chemical name.

The following are representative dihydroxycitrate esters: 2,3,4-trihydroxy-3-carboxypentane-1,5-dioate esters (dihydroxycitrate esters): trimethyl dihydroxycitrate, triethyl dihydroxycitrate, tripropyl dihydroxycitrate, tri-isopropyl dihydroxycitrate, triamyl dihydroxycitrate, trioctyl dihydroxycitrate, tri-isooctyl dihydroxycitrate, tribenzyl dihydroxycitrate and trinicotinyl dihydroxycitrate.

(b) Dihydroxyhomocitrate ester

Due to the positions of the second and third hydroxyl groups, there are three generic structures which can be represented as the following Formulas XVI, XVII and XVIII:

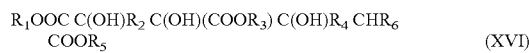

$$R_1OOC\ C(OH)R_2\ C(OH)(COOR_3)\ C(OH)R_4\ CHR_6\ COOR_5 \qquad (XVI)$$

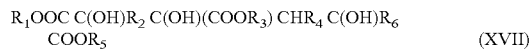

$$R_1OOC\ C(OH)R_2\ C(OH)(COOR_3)\ CHR_4\ C(OH)R_6\ COOR_5 \qquad (XVII)$$

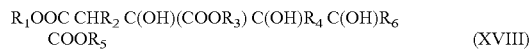

$$R_1OOC\ CHR_2\ C(OH)(COOR_3)\ C(OH)R_4\ C(OH)R_6\ COOR_5 \qquad (XVIII)$$

wherein in each of the Formulas XVI, XVII and XVIII, $R_1$, $R_3$ and $R_5$ are independently an alkyl group having 1 to 19 carbon atoms, or an aralkyl or aryl group having 6 to 19 carbon atoms; $R_2$, $R_4$ and $R_6$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The dihydroxyhomocitrate ester can be present as saturated or unsaturated, stereoisomeric or non-stereoisomeric, straight or branched chain or cyclic form.

If the generic structures of Formulas XVI, XVII or XVIII cannot cover a specific dihydroxyhomocitrate ester, the compound will be represented by its chemical name.

The following are representative dihydroxyhomocitrate esters:

2,3,4-trihydroxy-3-carboxyhexane-1,6-dioate esters; 2,3,5-trihydroxy-3-carboxyhexane-1,6-dioate esters and 3,4,5-trihydroxy-3-carboxyhexane-1,6-dioate esters (dihydroxyhomocitrate esters): trimethyl dihydroxyhomocitrate, triethyl dihydroxyhomocitrate, tripropyl dihydroxyhomocitrate, tri-isopropyl dihydroxyhomocitrate, triamyl dihydroxyhomocitrate, trioctyl dihydroxyhomocitrate, tri-isooctyl dihydroxyhomocitrate, tribenzyl dihydroxyhomocitrate and trinicotinyl dihydroxyhomocitrate.

(c) Dihydroxyhomoisocitrate ester

The generic structure can be represented as the following Formula XIX:

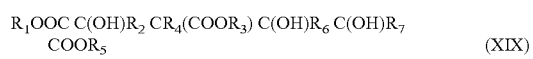

$$R_1OOC\ C(OH)R_2\ CR_4(COOR_3)\ C(OH)R_6\ C(OH)R_7\ COOR_5 \qquad (XIX)$$

wherein $R_1$, $R_3$ and $R_5$ are independently an alkyl group having 1 to 19 carbon atoms, or an aralkyl or aryl group having 6 to 19 carbon atoms; $R_2$, $R_4$, $R_6$ and $R_7$ are independently H, an alkyl group having 1 to 19 carbon atoms, or an aralkyl or aryl group having 6 to 19 carbon atoms; the H attached to any carbon atom can be substituted by I, F, Cl, Br or an alkoxyl group having 1 to 19 carbons. The dihydroxyhomoisocitrate ester can be present as saturated or unsaturated, stereoisomeric or non-stereoisomeric, straight or branched chain or cyclic form.

If the generic structure Formula XIX cannot cover a specific dihydroxyhomoisocitrate ester, the compound will be represented by its chemical name.

The following are representative dihydroxyhomoisocitrate esters: 2,4,5-trihydroxy-3-carboxyhexane-1,6-dioate esters (dihydroxyhomoisocitrate esters): trimethyl dihydroxyhomoisocitrate, triethyl dihydroxyhomoisocitrate, tripropyl dihydroxyhomoisocitrate, tri-isopropyl dihydroxyhomoisocitrate, triamyl dihydroxyhomoisocitrate, trioctyl dihydroxyhomoisocitrate, tri-isooctyl dihydroxyhomoisocitrate, tribenzyl dihydroxyhomoisocitrate and trinicotinyl dihydroxyhomoisocitrate.

In general, we have found that sensuous and sensational effects produced by the hydroxytricarboxylic ester are much stronger and last longer than that produced by hydroxydicarboxylic ester. In the same family group of hydroxytricarboxylic esters, we have also found that sensuous and sensational effects produced by the longer chain esters are much stronger and last longer than those produced by the shorter chain esters. For example, tripropyl citrate produces much stronger and longer-lasting sensuous and sensational effects than those produced by trimethyl citrate.

Cosmetic, pharmaceutical and other topical agents can also be incorporated into a composition of the present invention for synergetic or synergistic effects. The topical agents include, for example without limitation, hydroxyacids, ketoacids and related compounds; phenyl alpha acyloxyalkanoic acids and derivatives; N-acyl-aldosamines, N-acylamino acids and related N-acyl compounds; local analgesics and anesthetics; anti-acne agents; anti-bacterial agents; anti-yeast agents; anti-fungal agents; anti-viral agents; anti-infective agents; anti-dandruff agents; anti-dermatitis agents; anti-eczema agents; anti-histamine agents; anti-pruritic agents; anti-emetics; anti-motion sickness agents; anti-inflammatory agents; anti-hyperkeratotic agents; antiperspirants; anti-psoriatic agents; anti-rosacea agents; anti-seborrheic agents; hair conditioners and hair treatment agents; anti-aging and anti-wrinkle agents; anti-anxiety agents; anti-convulsant agents; anti-depressant agents; sunblock and sunscreen agents; skin lightening agents; depigmenting agents; astringents; cleansing agents; corn, callus and wart removing agents; skin plumping agents; skin volumizing agents; skin firming agents; matrix metalloproteinase (MMP) inhibitors; topical cardiovascular agents; wound-healing agents; gum disease or oral care agents; amino acids; peptides; dipeptides; tripeptides; glutathione and its derivatives; oligopeptides; polypeptides; carbohydrates; aminocarbohydrates; vitamins; corticosteroids; tanning agents; hormones and retinoids.

For synergetic or synergistic effects, the cosmetic, pharmaceutical and other topical agents also include, for example without limitation, abacavir, acebutolol, acetaminophen, acetaminosalol, acetazolamide, acetohydroxamic acid, acetylsalicylic acid, N-acylglutathione esters, acitretin, aclovate, acrivastine, actiq, acyclovir, adalimumab, adapalene, adefovir dipivoxil, adenosine, albuterol, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, p-aminobenzoic acid, aminocaproic acid, aminolevulinic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithromycin, bacitracin, beclomethasone dipropionate, bemegride, benazepril, bendroflumethiazide, benzocaine, benzonatate, benzophenone, benzoyl peroxide, benztropine, bepridil, betamethasone dipropionate, betamethasone valerate, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, carbamide peroxide, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, coal tar, coal tar extracts (LCD), cocaine, codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxypin, duloxetine, dyclonine, econazole, efalizumab, eflornithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, etidocaine, etomidate, famciclovir, famotidine, felodipine, fentanyl, ferulic acid, fexofenadine, flecainide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenytoin, physostigmine, pilocarpine, pimecrolimus, pimozide, pindolol, pioglitazone, pipamazine, piperonyl butoxide, pirenzepine, podofilox, podophyllin, povidone iodine, pramipexole, pramoxine, prazosin, prednisone, prenalterol, prilocaine, procainamide, procaine, procarbazine, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide (sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thioctic acid (lipoic acid), thioridazine, thiothixene, thymol, tiagabine, timolol, tinidazole, tioconazole, tirofiban, tizanidine, tobramycin, tocainide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, vardenafil, venlafaxine, verapamil, vitamin E acetate, voriconazole, warfarin, wood tar, xanthine, zafirlukast, zaleplon, zinc pyrithione, ziprasidone, zolmitriptan and zolpidem.

General Preparations

Compositions comprising a hydroxyl-oligocarboxylic ester, preferably a hydroxydicarboxylic ester, and more preferably a hydroxytricarboxylic ester, of the present invention can be formulated as solution, gel, lotion, cream, ointment, shampoo, spray, stick, pads, powder, masque, mouth rinse or wash, vaginal gel or preparation, or other form acceptable for use on mucocutaneous sites or the like, such as oral mucosa, lips, nostrils, vulva, vagina, penis, anus and nipples.

To prepare a solution composition, at least one hydroxy-oligocarboxylic ester, preferably a hydroxydicarboxylic ester, and more preferably a hydroxytricarboxylic ester, is dissolved in a solution prepared from water, ethanol, propylene glycol, butylene glycol, and/or other topically acceptable vehicle. The concentration of the hydroxy-oligocarboxylic ester can be about 0.1% to about 100% by weight of the total composition, with a preferred concentration of about 1% to about 40% by weight of the total composition, and with more preferred concentration of about 2% to about 20% by weight of the total composition.

To prepare a topical composition in lotion, cream or ointment form, the liquid form hydroxy-oligocarboxylic ester can be mixed directly with a desired base or can be first dissolved in ethanol, propylene glycol, and/or other solvent and the solution thus obtained is mixed with a desired base or pharmaceutically acceptable vehicle to make a lotion, cream or ointment. The concentration is the same as described above.

A topical composition of the instant invention can also be formulated in a gel form. A typical gel composition is formulated by the addition of a gelling agent, such as chitosan, methyl cellulose, ethyl cellulose, polyvinyl alcohol, polyquatemiums, hydroxyethylcellulose, hydroxypropylcellulose, hydroxypropylmethylcellulose, carbomer or ammoniated glycyrrhizinate, to a solution comprising the hydroxy-oligocarboxylic ester of the present invention. The preferred concentration of the gelling agent may be about 0.2% to about 2% by weight of the total composition.

To prepare a topical combination composition for synergetic or synergistic effects, a cosmetic, pharmaceutical or other topically active agent is incorporated into any one of the above compositions by dissolving or mixing the agent into the formulation.

Other forms of compositions for delivery of the compound of the present invention may readily be blended, prepared or formulated by those skilled in the art in view of the present disclosure.

A composition comprising a hydroxy-oligocarboxylic ester, preferably a hydroxydicarboxylic ester, and more preferably a hydroxytricarboxylic ester, can be topically applied to mucocutaneous organs or sites for sensual and sensational effects. The mucocutaneous organs or sites include lips, mouth, gum, nostrils, nipples, vulva, vagina, penis and anus. As noted above, the sensuous and sensational effects produced by the hydroxy-oligocarboxylic ester are quite different from the numbing effects induced by local anesthetics such as lidocaine and procaine. The sensuous and sensational effects produced by the hydroxy-oligocarboxylic ester generally last from a few minutes to a few hours. For example, a lipstick or lip balm comprising a hydroxydicarboxylic ester or preferably hydroxytricarboxylic ester can provide sensuous or sensational feeling after topical application to lips of a human subject. For instance, a cream or ointment containing 10% triethyl citrate, tripropyl citrate or triisopropyl citrate can be topically applied to lips. After one to two minutes, the lips will experience sensual and sensational pleasure with very mild anesthetic effects, and one feels that the lips are plumping up in size. Such feelings usually last for approximately 10 minutes to 2 hours.

Such actions on the nervous system are beneficial for many other cosmetic, dental and dermatological indications, such as to relieve itch or pain of lips, mouth, gum, nostrils, nipples, vulva, vagina, penis and anus, and for conditions associated with eczema, hemorrhoids, dry or aging-associated changes of the vulva and vagina.

A composition comprising a hydroxy-oligocarboxylic ester, preferably a hydroxydicarboxylic ester, and more preferably a hydroxytricarboxylic ester, can also be topically applied to mucocutaneous or skin lesions. For example, a cream or ointment containing 10% tripropyl citrate or triisopropyl citrate can be topically applied to eczematous or psoriatic lesions twice daily for 4 to 16 weeks. The itch associated with eczema or psoriasis usually disappears within a few minutes after topical application.

Another aspect of the invention is the use of a hydroxy-oligocarboxylic ester, preferably a hydroxydicarboxylic ester, and more preferably a hydroxytricarboxylic ester, to relieve pain, infections and/or inflammations associated with wound healing and disorders of mucocutaneous organs or sites such as canker sores and toothache. For the mouth diseases, the hydroxy-oligocarboxylic ester is formulated as a solution or gel form for mouth wash, gargle or rubbing.

In view of the anti-oxidant properties of the hydroxy-oligocarboxylic esters, yet another aspect of the invention is the use of them, and preferably anti-oxidant hydroxydicarboxylic ester or more preferably anti-oxidant hydroxytricarboxylic ester, as preventive care or treatment for damage, stinging or irritation of mucocutaneous organs or sites, skin, hair or nails caused by sunlight, chemicals, laser treatment, free radicals, electromagnetic radiation, ionizing radiation such as alpha rays, beta rays, X-rays, gamma rays or other oxidative damages.

Preferred embodiments of the invention will now be described in more detail with respect to the following specific, non-limiting examples.

EXAMPLE 1

Ethyl glycolate 10 g was mixed with 90 g ointment prepared from white petrolatum 50 parts, mineral oil 40 parts and white beeswax 10 parts. The composition thus prepared contained 10% ethyl glycolate in a hydrophobic ointment that was not washable with water (a water-non-washable ointment).

A male subject, age 73, topically applied the above 10% ethyl glycolate ointment on his lips. There was no sensual or sensational feelings during the next 30 minutes. This result shows that a hydroxy-monocarboxylic ester does not produce any actions on the nerve in mucocutaneous sites.

EXAMPLE 2

L-Ethyl lactate 10 g was mixed with 90 g ointment prepared from white petrolatum 50 parts, mineral oil 40 parts and white beeswax 10 parts. The composition thus prepared contained 10% L-ethyl lactate in water-non-washable ointment. A male subject, age 73, topically applied the above 10% L-ethyl lactate ointment on his lips. There was no sensual or sensational feelings during the next 30 minutes. This result shows that a different hydroxy-monocarboxylic ester does not produce any actions on the nerve in mucocutaneous sites.

EXAMPLE 3

DL-Diethyl malate 10 g was mixed with 90 g ointment prepared from white petrolatum 50 parts, mineral oil 40 parts and white beeswax 10 parts. The composition thus prepared contained 10% DL-diethyl malate in a water-non-washable ointment.

A male subject, age 73, topically applied the above 10% DL-diethyl malate ointment on his lips. After one to two minutes, the lips experienced sensual and plumping feelings which lasted for about 10 to 20 minutes. Such action on the nerves of the lips shows a hydroxydicarboxylic ester can provide beneficial effect, representative of other beneficial effects for various cosmetic conditions and dermatological indications.

EXAMPLE 4

D-Diethyl tartarate 10 g was mixed with 90 g ointment prepared from white petrolatum 50 parts, mineral oil 40 parts and white beeswax 10 parts. The composition thus prepared contained 10% D-diethyl tartarate in a water-non-washable ointment.

A male subject, age 73, topically applied the above 10% D-diethyl tartarate ointment on his lips. After one to two minutes, the lips experienced slight sensual and plumping feelings which lasted for about 10 to 20 minutes. Such action on the nerves of the lips shows that a dihydroxydicarboxylic ester can provide a beneficial effect, representative of other beneficial effects for various cosmetic conditions and dermatological indications.

EXAMPLE 5

L-Diethyl tartarate 10 g was mixed with 90 g ointment prepared from white petrolatum 50 parts, mineral oil 40 parts and white beeswax 10 parts. The composition thus prepared contained 10% L-diethyl tartarate in a water-non-washable ointment. A male subject, age 73, topically applied the above 10% L-diethyl tartarate ointment on his lips. After one to two minutes, the lips experienced slight sensual and plumping feelings which lasted for about 10 to 20 minutes. Such action on the nerves of the lips shows that a dihydroxydicarboxylic ester can provide a beneficial effect, representative of other beneficial effects for various cosmetic conditions and dermatological indications.

EXAMPLE 6

Triethyl citrate 10 g and propylene glycol 10 ml were mixed with hydrophilic ointment or oil-in-water emulsion 80 g. The composition thus prepared contained 10% triethyl citrate in a water-soluble oil-in-water emulsion.

A male subject, age 73, topically applied the above 10% triethyl citrate cream on his lips. After one to two minutes, the lips experienced sensual and plumping feelings which lasted for about 20-30 minutes. Such action on the nerves of the lips shows that a monohydroxytricarboxylic ester can provide a beneficial effect, representative of other beneficial effects for various cosmetic conditions and dermatological indications.

EXAMPLE 7

Triethyl citrate 10 g was mixed with 90 g ointment prepared from white petrolatum 50 parts, mineral oil 40 parts and white beeswax 10 parts. The composition thus prepared contained 10% triethyl citrate in a water-non-washable ointment.

Seven volunteer subjects, four males and three females, topically applied the above 10% triethyl citrate ointment on their lips. After one to two minutes, the lips experienced sensual and plumping feelings which lasted for about 20 to 30 minutes. Such action on the nerves of the lips shows that a monohydroxytricarboxylic ester in a different formulation than in Example 6 and used by several subjects can provide a beneficial effect, representative of other beneficial effects for various cosmetic conditions and dermatological indications.

EXAMPLE 8

Triethyl citrate 10 g was mixed with 90 g ointment prepared from white petrolatum 50 parts, mineral oil 40 parts and white beeswax 10 parts. The composition thus prepared contained 10% triethyl citrate in a water-non-washable ointment.

A male subject, age 73, having atopic eczema with severe itching skin topically applied the above 10% triethyl citrate ointment to the itching skin on his right lower leg. After a few minutes, the itch stopped, and the skin remained free of itch for the ensuing 4 hours. This result shows that a monohydroxytricarboxylic ester can provide beneficial anti-itching effects, representative of other beneficial effects for various cosmetic conditions and dermatological indications.

EXAMPLE 9

Trimethyl citrate 10 g was mixed with 90 g ointment prepared from white petrolatum 50 parts, mineral oil 40 parts and white beeswax 10 parts. The composition thus prepared contained 10% trimethyl citrate in a water-non-washable ointment.

A male subject, age 73, topically applied the above 10% trimethyl citrate ointment on his lips. After one to two minutes, the lips experienced very slight sensual and plumping feelings. Such action on the nerves of the lips shows that another monohydroxytricarboxylic ester can provide a beneficial effect, representative of other beneficial effects for various cosmetic conditions and dermatological indications.

EXAMPLE 10

Lidocaine 5 g was dissolved in warm propylene glycol 20 ml, and the solution thus obtained was mixed with 75 g ointment prepared from white petrolatum 50 parts, mineral oil 40 parts and white beeswax 10 parts. The composition thus prepared contained 5% lidocaine in a water-non-washable ointment.

A male subject, age 73, topically applied the above 5% lidocaine ointment on his lips. After a few minutes, the lips felt numb and the insensible numbing effect lasted for several hours. Such numbing or anesthetic effect was completely different from the sensual and sensational effects produced by a hydroxy-oligocarboxylic ester.

EXAMPLE 11

Tripropyl citrate 10 g was mixed with 90 g ointment prepared from white petrolatum 50 parts, mineral oil 40 parts and white beeswax 10 parts. The composition thus prepared contained 10% tripropyl citrate in a water-non-washable ointment.

A male subject, age 73, topically applied the above 10% tripropyl citrate ointment on his lips. After a few minutes, the lips experienced sensual and sensational feelings which lasted for about 1.5 to 2 hours. Such action on the nerves of the lips shows that another monohydroxytricarboxylic ester can provide a beneficial effect, representative of other beneficial effects for various cosmetic conditions and dermatological indications.

EXAMPLE 12

Tripropyl citrate 10 g and propylene glycol 20 ml were mixed with hydrophilic ointment or oil-in-water emulsion 70 g. The composition thus prepared contained 10% tripropyl citrate in water-soluble oil-in-water emulsion.

A male subject, age 73, having atopic eczema with severe itching skin, topically applied the above 10% tripropyl citrate cream on his right leg with itchy eczematous lesions. After a few minutes, the itch disappeared completely, and the skin remained free of itch for the ensuing 4 hours. This result shows that a different monohydroxytricarboxylic ester in a different formulation can provide beneficial anti-itching effects, representative of other beneficial effects for various cosmetic conditions and dermatological indications.

EXAMPLE 13

Tri-isopropyl citrate 10 g was mixed with 90 g ointment prepared from white petrolatum 50 parts, mineral oil 40 parts and white beeswax 10 parts. The composition thus prepared contained 10% tri-isopropyl citrate in a water-non-washable ointment.

A male subject, age 74, topically applied the above 10% tri-isopropyl citrate ointment on his lips. After a few minutes, the lips experienced sensual and sensational feelings which lasted for about an hour. This result shows that a different monohydroxytricarboxylic ester can provide a beneficial effect, representative of other beneficial effects for various cosmetic conditions and dermatological indications.

EXAMPLE 14

Tribenzyl citrate 10 g was mixed with 90 g ointment prepared from white petrolatum 50 parts, mineral oil 40 parts and white beeswax 10 parts. The composition thus prepared contained 10% tribenzyl citrate in a water-non-washable ointment.

A male subject, age 74, topically applied the above 10% tribenzyl citrate ointment on his lips. After a few minutes, the lips experienced slight sensual and sensational feelings. This result shows that a different, aromatic monohydroxytricarboxylic ester can provide a beneficial effect, representative of other beneficial effects for various cosmetic conditions and dermatological indications.

EXAMPLE 15

A typical combination composition was formulated as follows. Hydrocortisone-17-valerate 0.2 g was dissolved in liquid triethyl citrate 15 g and propylene glycol 10 ml. The solution thus obtained was mixed with 74.8 g ointment prepared from white petrolatum 50 parts, mineral oil 40 parts and white beeswax 10 parts. The composition thus prepared contained 15% triethyl citrate and 0.2% hydrocortisone-17-valerate in a water-non-washable ointment.

A male subject, age 74, topically applied the above ointment on his itchy and eczematous skin. After a few minutes the itch disappeared, and the composition had in addition an anti-inflammatory effect. The results showed that the composition would be beneficial for topical treatment of pruritus, eczema and other inflammatory skin diseases.

EXAMPLE 16

Another typical combination composition was formulated as follows. Menthol 1 g was dissolved in liquid tri-isopropyl citrate 10 g and propylene glycol 10 ml. The solution thus obtained was mixed with 79 g ointment prepared from white petrolatum 50 parts, mineral oil 40 parts and white beeswax 10 parts. The composition thus prepared contained 10% tri-isopropyl citrate and 1% menthol in a water-non-washable ointment.

A male subject, age 74, topically applied the above ointment on his itchy and eczematous skin. After a few minutes the itch diminished, and the composition had a soothing effect on the eczematous lesions. The results showed that the composition would be beneficial for topical treatment of pruritus, eczema and other inflammatory skin diseases.

EXAMPLE 17

Another typical combination composition was formulated as follows. Diphenhydramine hydrochloride 58 g (0.2 mole) was dissolved in water 100 ml, and 5N NaOH 40 ml (0.2 mole) was added slowly with stirring. Diphenhydramine free base was formed as oily white precipitates. Without isolation of the free base, N-acetyl-L-proline 48 g (0.3 mole) and N-acetyl-D-glucosamine 44 g (0.2 mole) were added with stirring into the oily mixture, and the mixture became a clear solution. Propylene glycol 100 ml and water 50 ml were added to make total volume 400 ml (444 g). This formulation contained diphenhydramine 14.5%, N-acetyl-L-proline 12% and N-acetyl-D-glucosamine 11% in a propylene glycol/water solution. The above formulation 22 g and tribenzyl citrate 10 g were mixed with hydrophilic ointment or oil-in-water cream 68 g. The composition thus prepared had pH 3.8 and contained 10% tri-benzyl citrate, 3% diphenhydramine, 2.6% N-acetyl-L-proline and 2.4% N-acetyl-D-glucosamine in a water-washable cream.

A male subject, age 74, topically applied the above composition on his itchy and eczematous skin. After a few minutes, the itch disappeared. The result showed that the composition would be beneficial for topical treatment of pruritus, eczema and other inflammatory skin diseases.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for producing an effect in feeling of arousing or plumping on the lips of a subject, wherein the method comprises topically applying to the lips a composition comprising about 1% to about 40% by weight of the total composition a citrate ester, wherein the citrate ester is selected from the group consisting of trimethyl citrate, triethyl citrate, tripropyl citrate and tri-isopropyl citrate.

2. The method of claim 1, wherein the subject is a human.

3. The method of claim 1, wherein the citrate ester is triethyl citrate.

4. The method of claim 1, wherein the citrate ester is tripropyl citrate.

5. The method of claim 1, wherein the citrate ester is tri-isopropyl citrate.

6. The method of claim 1, wherein the citrate ester is trimethyl citrate.

7. The method of claim 1, wherein the composition comprises about 2% to about 20% by weight of the total composition the citrate ester.

* * * * *